United States Patent [19]
Lucki

[11] 3,959,400
[45] May 25, 1976

[54] OLEFIN DIMERIZATION
[75] Inventor: Stanley J. Lucki, Runnemede, N.J.
[73] Assignee: Mobil Oil Corporation, New York, N.Y.
[22] Filed: Dec. 23, 1974
[21] Appl. No.: 535,543

Related U.S. Application Data
[63] Continuation-in-part of Ser. No. 402,565, Oct. 1, 1973, abandoned.

[52] U.S. Cl. ............... 260/683.15 R; 252/466 R
[51] Int. Cl.$^2$ ............................................. C07C 3/14
[58] Field of Search .............. 260/683.15 R, 683.15

[56] References Cited
UNITED STATES PATENTS

| | | | |
|---|---|---|---|
| 2,794,842 | 6/1957 | Hogan et al. | 260/683.15 R |
| 3,238,272 | 3/1966 | Nixon | 260/683.15 R |
| 3,442,964 | 5/1969 | Oldham | 260/683.15 R |
| 3,527,839 | 9/1970 | Glockner et al. | 260/683.15 R |
| 3,557,242 | 1/1971 | Sampson et al. | 260/683.15 R |

*Primary Examiner*—D. Horwitz
*Attorney, Agent, or Firm*—Charles A. Huggett; Raymond W. Barclay; Dennis P. Santini

[57] ABSTRACT

A process is provided for dimerization of light olefins comprising from 2 to 4 carbon atoms which comprises contacting same at a weight hourly space velocity of from about 0.1 to about 10, a temperature of from about 32°F to about 350°F and a pressure of from about 200 psig to about 1000 psig with a catalyst of alumina having intimately combined therewith from about 2 to about 5 weight percent nickel and from about 1 to about 3 weight percent sulfur as a result of impregnation with nickel sulfate, said alumina being gamma, eta or a mixture thereof and said catalyst having been calcined at a temperature of from 750°F to about 1150°F in an inert oxygen-free, non-reducing atmosphere.

11 Claims, No Drawings

OLEFIN DIMERIZATION

CROSS REFERENCE TO RELATED APPLICATION

This is a continuation-in-part of application Ser. No. 402,565, filed Oct. 1, 1973, now abandoned.

BACKGROUND OF THE INVENTION

1. Field of the Invention

This invention is directed to the dimerization of olefins comprising from 2 to 4 carbon atoms, e.g. propylene, wherein said dimerization is performed in the presence of a catalyst of gamma and/or eta alumina having been impregnated with nickel sulfate and calcined at a temperature as low as 750°F to as high as 1150°F in an inert oxygen-free non-reducing atmosphere, e.g. helium, nitrogen and combinations thereof. The amount of nickel impregnated on said alumina is critical, with decreased activity observed when the nickel content of the catalyst is less than 2 weight percent and with decreased selectivity observed when the nickel content of the catalyst is more than 5 weight percent. The most advantageous results are obtained when the nickel content of the catalyst is between about 2 weight percent and about 3 weight percent. Said catalyst, when used in the process of the present invention, is characterized by exceptionally long catalyst life, capability of affording high yields of desired dimer products with high selectivity, e.g. propylene dimer ($C_6^=$) when propylene is the feed olefin, and being easily and effectively regenerated, when necessary, without substantial loss in activity. The specific catalyst for use herein is stable through multiple regenerations.

2. Discussion of the Prior Art

Dimerization and polymerization of compounds such as ethylene and propylene using catalysts other than that of this invention is known in the art. For example, an article appearing in the April, 1955, issue of *Industrial and Engineering Chemistry*, Volume 47, pages 752–757, disclosed that a catalyst of nickel oxides impregnated on silica-alumina may be useful for the polymerization of light olefins, such as those contained in a refinery cracked gas, e.g. ethylene. The article further disclosed that active catalysts were obtained by impregnation of the silica-alumina with solutions of nickel chloride or nickel sulfate. The article emphasized, however, that the most active polymerization catalyst was prepared by using an impregnation solution containing about 40 weight percent nickel nitrate hexahydrate to impregnate the silica-alumina.

Unfortunately, in the process of dimerization of light olefins as herein set forth, alumina impregnated with nickel nitrate has no activity (demonstrated by example hereinafter).

Also a Russian article appearing in *Zhurnal Organicheskoi Khimii*, Vol. 8, No. 3, pages 650–651 (March, 1972), disclosed the use of nickel chloride deposited on an aluminosilicate or aluminum oxide, which has been activated by heating under vacuum or inert gas, for dimerization of ethylene and propylene. In such a process, however, it is known (and shown by specific example hereinafter) that the catalyst ages rather rapidly with regeneration causing substantial decline in catalyst activity. Further, the above nickel chloride catalyst requires a minimum of about 950°F for activation, whereas the catalyst for use herein may be activated at lower temperatures of, for example, as low as 750°F.

U.S. Pat. No. 2,794,842 teaches catalytic polymerization of olefins in the presence of nickel sulfate-promoted catalysts. That patent teaches the necessity in its process of activating the catalyst for use therein by heating in an oxygen-containing atmosphere. It further teaches the catalyst for use therein as having from 0.1 to 10 weight percent nickel. Applicant has discovered that the use of the present catalyst, i.e. gamma and/or eta alumina being intimately combined with a very limited range of nickel, e.g. 2 to 5 weight percent, and sulfur, e.g. 1 to 3 weight percent, as a result of impregnation with nickel sulfate in appropriate amount and being calcined at a temperature of from 750°F to 1150°F in an inert oxygen-free, non-reducing atmosphere, provides high conversion of olefin feed with high selectivity to dimer. This, of course, is at the expense of polymer formation in the process. By the present process, alkenes are produced having exactly twice the number of carbon atoms and hydrogen atoms as the alkene feed in high selectivity and conversion. If an oxygen-containing or a reducing atmosphere is used in calcining the catalyst or if the catalyst contains less than 2 or more than 5 weight percent nickel, lower conversion and/or selectivity results.

U.S. Pat. No. 3,557,242 teaches a process for dimerization of olefins using a silica-alumina catalyst incorporating nickel oxide or a nickel salt, wherein the proportion of alumina in the catalyst is within the range of from only 0.1 to 10 percent by weight. That patent teaches that increasing the alumina content of the catalyst over the 10 percent maximum destroys dimer selectivity. Applicant has discovered that dimer selectivity is enhanced when the catalyst employed is a 100 percent alumina structure intimately combined with nickel and sulfur as above described.

SUMMARY OF THE INVENTION

This invention contemplates a process for effecting high yield dimerization of olefins of 2 to 4 carbon atoms which comprises contacting same with a catalyst of gamma and/or eta alumina having intimately combined therewith from about 2 to about 5 weight percent nickel and from about 1 to about 3 weight percent sulfur as a result of impregnation with nickel sulfate, said catalyst having been calcined at a temperature of from 750°F to about 1150°F in an inert oxygen-free, non-reducing atmosphere, and said contacting being carried out at an olefin feed weight hourly space velocity of from about 0.1 to about 10, a reaction temperature of from about 32°F to about 350°F and a reaction pressure of from about 200 psig to about 1000 psig.

DESCRIPTION OF SPECIFIC EMBODIMENTS

The olefin feedstock for the process of the present invention may be one or more of the unsaturated open-chain hydrocarbons containing at least one carbon-carbon double bond and having 2 to 4 carbon atoms per molecule, such as, for example, ethylene, propylene and 1-butene.

The olefin feedstock may be utilized in the process of this invention in relatively pure olefinic form or may be in admixture with one or more other non-reactive organic, e.g. hydrocarbon, compounds, possibly functioning as diluents. Non-limiting examples of the other non-reactive organic compounds which may be present in such an admixture include saturated hydrocarbons from 3 to 10 carbon atoms such as propane, butane and n-hexane. One possible utility of the non-reactive material present in admixture with the reactive olefin feed is to act as a catalyst quench in favor of lower reaction temperatures because of the exothermic reaction occurring during the present process.

The operating conditions employed in the present process are critical and will be dependent, at least in part, on the specific dimerization reaction being effected. Such conditions as temperature, pressure, space velocity, and presence of non-reactive organic compounds and their interrelation, one with the other, will have an important influence on the process. Accordingly, the manner in which these conditions influence the conversion and distribution of the resulting dimerized products and the rate of catalyst deactivation will be described hereinafter.

The olefin feed weight hourly space velocity utilized in the present process is from about 0.1 to about 10 with a preferred range of from about 0.2 to about 4, depending upon the other operating conditions employed and the desired yield and selectivity obtainable. Of course, when the olefin feed is supplied to the reaction of the present process in admixture with one or more non-reactive components, i.e. organic compounds hereinbefore discussed, the total feed (reactive olefin plus non-reactive components) weight hourly space velocity may be within the rather large range of from about 0.1 to about 50 or more, depending to a large extent upon the amount of non-reactive material present in relation to the reactive olefin feed.

The process of the present invention is effective at temperatures as low as 32°F with relatively high conversion, for example greater than 95 percent, of the olefin feed. However, since costly cooling means must be employed in order to maintain low temperature during this exothermic process, a preferred lower temperature is about 100°F. The process is effective at temperatures as high as 350°F with excellent conversion and dimer selectivity, with a preferred process temperature maximum of about 200°F.

Since it is highly desirable in this process to maintain the olefin feed in the liquid state, reaction pressures may be in the range of from about 200 psig to about 1000 psig, with a preferred range of from about 250 psig to about 600 psig, depending, of course, upon the particular reactant olefin employed as feed; its degree of dilution, if diluted; the non-reactive material used as diluent, if diluent present; reaction temperature and the like.

The catalyst for use in the present invention is gamma alumina, eta alumina or a combination of gamma and eta alumina which has intimately combined therewith from about 2 to about 5 weight percent nickel and from about 1 to about 3 weight percent sulfur as a result of impregnation with nickel sulfate. In a preferred embodiment of the present process, the catalyst has from about 2 to about 3 weight percent nickel and from about 1 to about 1.7 weight percent sulfur.

The alumina base of the catalyst useful herein may be one or a mixture of two of the presently available alumina materials, such as, for example, gamma alumina alone, eta alumina alone or a mixture of gamma and eta alumina. Selection of an alumina for use herein may depend upon availability and cost, as catalysts prepared with either, for example, gamma alumina or eta alumina have shown that they can provide propylene conversion of 95 percent with $C_6^=$ selectivity of greater than 80 percent.

The catalyst for use in the present process may be suitably prepared by the general process of first freshly calcining according to methods known in the art, e.g. at 950°F for 16 hours, a quantity of gamma and/or eta alumina of, for example, 30/60 mesh, and then rapidly adding said alumina to a quantity of an aqueous solution of nickel sulfate, e.g. a solution of about 4.5 to about 13 percent $NiSO_4.6H_2O$ at room temperature. The mixture may then be allowed to stand for a time, e.g. 2 minutes to an hour, after which the unsorbed portion of solution is withdrawn through a medium porosity, glass fritted funnel with vacuum applied. The impregnated alumina may then be transferred to an evaporating means, such as, for example, an evaporating dish placed in an oven set at, for example 210°F to 240°F, and dried for a time of, for example, 1 to 5 hours. The dried catalyst material must be activated by being calcined by heating to a temperature of from 750°F to about 1150°F in an inert oxygen-free, non-reducing atmosphere of, for example, helium, nitrogen and combinations thereof. The calcined and, thereby, activated catalyst will contain from about 2 to about 5 weight percent nickel and from about 1 to about 3 weight percent sulfur.

Also, as an aid in maintaining a desired reaction temperature, catalyst materials as above prepared may be diluted with a low surface area form, e.g. tabular, of an inorganic oxide or clay agent. Non-limiting examples of such catalyst diluting agents include alumina, zirconia, silica, magnesia, thoria, titania, boria and combinations thereof. Further examples of such agents are the clay materials bentonite and kieselguhr.

The process of this invention is conducted such that dimerization of an olefin comprising from 2 to 4 carbon atoms, exemplified by propylene, is carried out in preferably the liquid-phase by contact in a reaction zone, such as, for example, a fixed bed of catalyst as above prepared, under effective dimerization conditions as above defined. Dimerization of olefins hereby, that is producing compounds having exactly twice the number of carbon and hydrogen atoms as the olefin feed, is accomplished in high conversion and selectivity at the expense of less desireable polymer product, i.e. product having many times more carbon and hydrogen atoms than the olefin feed.

The catalysts prepared according to the above description were tested in a down flow, bench scale, pressure unit.

The catalyst bed was ½ inch in diameter, 4½ inches long, and contained 2 cc of 20/30 mesh catalyst that had been previously mixed with 8 cc 30/60 mesh inert tabular alumina. The reactor was water jacketed and maintained at the proper operating temperature by means of a constant temperature water bath.

The reactor was flushed with helium and pressured to 400 psig and given a 30 minute purge at 300 cc/minute during a temperature lineout. Helium was then discontinued and a propane/propylene charge was introduced into the reactor.

Lineout time of 90 minutes was followed by a balance run of 30 minutes. Total product was trapped at liquid nitrogen temperatures and after weathering to room temperature in a known volume apparatus, the gaseous and liquid products were analyzed chromatographically.

The following specific examples will serve to illustrate the process of this invention, without unduly limiting same.

EXAMPLE 1

Fifteen ml. of 20/30 mesh gamma alumina, freshly calcined in air for 16 hours at 950°F and cooled to room temperature, was rapidly added to 25 ml of an 8.0 weight percent aqueous solution of $NiSO_4 \cdot 6H_2O$ contained in a medium porosity, glass fritted funnel at room temperature. The resulting mixture was allowed to stand for 10 minutes and then vacuum was applied to the funnel, resulting in the removal of excess solution of nickel salt.

The nickel sulfate impregnated alumina was then placed in an oven and air-dried for three hours at 230°F. Drying was followed by heating the impregnated alumina to 950°F at 18°F/minute in a stream of an inert oxygen-free, non-reducing atmosphere (i.e. held at a gas/catalyst volume ratio of 30/1.) The duration of calcination at 950°F was 16 hours.

The calcined catalyst was shown by analysis (ignition basis) to contain 2.9 weight percent Ni and 1.6 weight percent S (analysis of S as validly made since the Ni/S stoichiometric ratio on the catalyst is identical to the Ni/S ratio in $NiSo_4$).

The nickel sulfate impregnated catalyst material prepared in Example 1 was evaluated in the hereinbefore described testing method with the propane/propylene charge being used in the ratio of 39.6/60.4, propane weight percent/propylene weight percent. The reaction temperature was 105°F, the weight hourly space velocity of the propylene feedstock was 1.0, the reaction pressure was maintained at 400 psig and the weight percent conversion of the propylene was 95.8, with 83.1 percent of the product being propylene dimer ($C_6^=$).

EXAMPLE 2

To demonstrate the necessity that the nickel sulfate impregnated alumina catalyst for use herein must be calcined in a non-reducing atmosphere of, for example, helium, nitrogen or combinations thereof, a nickel sulfate impregnated alumina was prepared as in Example 3(hereinafter), dried and heated to 930°F at 18°F/minute in a stream of hydrogen. The duration of calcination was 2 hours.

The calcined catalyst was shown by analysis to contain 2.6 weight percent Ni and 0.91 weight percent S.

The catalyst prepared in Example 2 was then tested as in Example 1. Only 0.8 percent conversion of the propylene feed resulted.

EXAMPLE 3

Fifteen ml. of 20/30 mesh gamma alumina, freshly calcined in air for 16 hours at 950°F and cooled to room temperature, was rapidly added to 25 ml of an 8.0 weight percent aqueous solution of $NiSO_4 \cdot 6H_2O$ contained in a funnel as used in Example 1. The resulting mixture was allowed to stand for 10 minutes and then the excess solution of nickel salt was removed as in Example 1.

The catalyst thus prepared was then air-dried in an oven at 230°F for 3 hours. Drying was followed by heating the impregnated alumina to 940°F at 18°F/minute in a stream of helium at a gas/catalyst volume ratio of 30/1. The duration of calcination at 940°F was 65 hours.

The calcined catalyst was shown by analysis to contain approximately 2.97 weight percent Ni and 1.72 weight percent S.

When the catalyst prepared in Example 3 was evaluated in the hereinbefore defined testing method with a weight hourly space velocity of the propylene feed maintained at 1.0, a propane/propylene charge of 36/64 (weight percent ratio), a reaction temperature of 150°F and a reaction pressure of 420 psig, propylene conversion of 98.3 percent resulted, with 69.5 percent propylene dimer ($C_6^=$) in the reaction product.

EXAMPLE 4

Another quantity of catalyst material for use herein was prepared as in Example 1 except for the fact that the aqueous solution of $NiSO_4 \cdot 6H_2O$ was a 6.4 weight percent solution. The calcined catalyst material prepared hereby was shown by analysis (ignition basis) to contain 2.5 weight percent Ni and 1.3 weight percent S.

The nickel sulfate impregnated catalyst material prepared in Example 4 was evaluated in the same testing method used for the catalyst material of Example 1, except that the propane/propylene charge had a ratio of 35.3/64.7, propane weight percent/propylene weight percent, the reaction temperature was 103°F and the weight hourly space velocity of the propylene feedstock was maintained at 0.5. The weight percent conversion of propylene was 96.5, with 87.0 percent of the product being propylene dimer.

EXAMPLE 5

Another quantity of catalyst material for use herein was prepared as in Example 1, except for the fact that the aqueous solution of $NiSO_4 \cdot 6H_2O$ was a 5.1 weight percent solution. The calcined material prepared hereby was shown by analysis to contain 2.1 weight percent Ni and 1.1 weight percent S.

The catalyst material prepared in Example 5 was evaluated in the same testing method used for the catalyst material of Example 4, except that the reaction temperature was 145°F and the weight hourly space velocity was 1.1. The weight percent conversion of propylene was 86.5, with 89.4 percent of the product being propylene dimer.

EXAMPLE 6

A further quantity of catalyst material was prepared in order to determine a lower limit requirement for the nickel content of the catalyst for use in the present method. This quantity of catalyst material was prepared as in Example 1, except for the fact that the $NiSO_4 \cdot 6H_2O$ solution was only 4.0 weight percent. The calcined material prepared hereby was shown by analysis to contain 1.7 weight percent Ni and 0.9 weight percent S.

The catalyst material prepared in Example 6 was evaluated in the same manner as was the catalyst material of Example 5, except that the reaction temperature was 144°F and the weight hourly space velocity was 1.0. The weight percent conversion of propylene was only 37.2.

EXAMPLE 7

In order to determine an upper limit requirement for the nickel content of the catalyst for use in the present process, a quantity of catalyst material was prepared as in Example 1, except for the fact that the $NiSO_4 \cdot 6H_2O$ solution was 40.0 weight percent. The calcined material prepared hereby was shown by analysis to contain 8.3 weight percent Ni and 4.5 weight percent S.

The catalyst material prepared in Example 7 was evaluated in the same manner as the catalyst material of Example 5, except that the reaction temperature was 142°F and the weight hourly space velocity was 2.5. The weight percent conversion of propylene was 99.5, but the percent of the product which was propylene dimer was only 49.4.

EXAMPLES 8–18

A number of separate quantities of the catalyst material for use in the present process were prepared as in Example 4. They each had a nickel content of 2.5 weight percent and a sulfur content of 1.3 weight percent after activation by calcination for 16 hours at 950°F in helium. The separate quantities of catalyst material were each evaluated in the same manner as the catalyst material of Example 4. Said evaluations, herein referred to as Examples 8–18, were conducted with reaction temperature and weight hourly space velocity as indicated in Table I, hereinafter presented. The results of the evaluations are also presented in Table I.

TABLE I

| Example Number | Dimerization Process Conditions & Results | | | |
|---|---|---|---|---|
| | Temp.,°F | WHSV | Conversion | Selectivity |
| 8 | 117 | 1.0 | 94.0 | 88.2 |
| 9 | 119 | 1.0 | 92.9 | 89.7 |
| 10 | 129 | 1.1 | 91.5 | 89.4 |
| 11 | 150 | 2.5 | 88.2 | 82.8 |
| 12 | 106 | 1.0 | 92.0 | 89.3 |
| 13 | 125 | 0.6 | 97.1 | 84.0 |
| 14 | 150 | 2.6 | 87.9 | 87.4 |
| 15 | 106 | 0.9 | 92.1 | 88.6 |
| 16 | 106 | 1.0 | 93.6 | 88.0 |
| 17 | 105 | 0.6 | 96.1 | 88.2 |
| 18 | 104 | 0.45 | 97.2 | 86.4 |

EXAMPLE 19

A quantity of catalyst material for use herein was prepared as in Example 5. It contained 2.1 weight percent Ni and 1.1 weight percent S after activation by calcination for 16 hours at 950°F in helium. The material prepared hereby was evaluated in the same manner as the catalyst material of Example 5, except that the reaction temperature was 143°F. The weight percent propylene conversion was 80.0, with 91.8 percent of the product being propylene dimer.

EXAMPLE 20

In seeking the ideal catalyst for the present process, the prior art catalyst composition of alumina impregnated with nickel nitrate (see discussion of prior art set forth hereinbefore) was prepared and evaluated as follows:

Fifteen ml. of 20/30 mesh gamma alumina, freshly calcined in air for 16 hours at 950°F and cooled to room temperature, was rapidly added to 25 ml of a 15.6 weight percent aqueous solution of $Ni(NO_3)_2.6H_2O$ contained in a funnel as used in Example 1. The resulting mixture was allowed to stand 10 minutes and the excess nickel salt was removed as in Example 1.

The nickel nitrate impregnated alumina was then placed in an oven and air-dried for 3 hours at 230°F. Drying was followed by heating the impregnated alumina to 950°F at 18°F/minute in a stream of helium at a gas/catalyst volume ratio of 30/1. The duration of calcination at 950°F was 2 hours.

The calcined catalyst was shown by analysis to contain 3.6 weight percent Ni.

The nickel nitrate impregnated catalyst material prepared in Example 20 was evaluated by the testing method of Example 1 and the weight percent conversion of propylene was only 0.3.

EXAMPLE 21

Fifteen ml. of 20/30 mesh gamma alumina was prepared as in Example 1 and rapidly added to 25 ml. of a 29.8 weight percent solution of, in this example, $NiCl_2.6H_2O$ contained in a funnel as used in Example 1. The mixture was allowed to stand and excess nickel salt was removed as in Example 1.

The nickel chloride impregnated alumina, known in the art as being useful for olefin dimerization, was then dried in an oven at 230°F for 3 hours, heated to 950°F at 18°F/minute in a stream of helium and calcined at the 950°F temperature for 2 hours.

The calcined catalyst prepared in Example 21 contained 3.7 weight percent Ni and 2.8 weight percent Cl. It was evaluated as in Example 1 with the reaction temperature maintained at 150°F. The process was effective for only 8.5 days with an average conversion of 91 percent and average propylene dimer selectivity of 88 percent.

To further demonstrate the dramatic improvement of the process of the present invention using the hereinbefore defined catalyst, i.e. alumina impregnated with nickel sulfate, in relation to use of a prior art catalyst of alumina impregnated with nickel chloride, Examples 22 and 23 are presented.

EXAMPLE 22

The prior art catalyst of Example 21 was regenerated following the 8.5 day test run by the procedure of heating in nitrogen for 16 hours at 950°F. The regenerated catalyst placed back on test was effective for 3.8 days thereafter and was regenerated a second time by heating in nitrogen for 2 hours at 950°F. The catalyst thus regenerated for a second time was again placed on test for 3.4 days. The results of the total test, i.e. fresh catalyst of Example 21 for 8.5 days, regenerated (one time) catalyst for 3.8 days and regenerated (two times) catalyst for 3.4 days, is presented in Table II.

TABLE II

| Aging/Regeneration Study of NiCl Dimerization Catalyst in Present Process | | | | |
|---|---|---|---|---|
| Catalyst of Example | WHSV[1] | Days on Test Run | Conversion[2] | Selectivity[3] |
| 22 (fresh) | 1.0 | 8.5 | 91 | 88 |
| 22 (once regenerated) | 1.0 | 3.8 | 72 | 91 |

TABLE II-continued

Aging/Regeneration Study of NiCl Dimerization Catalyst in Present Process

| Catalyst of Example | WHSV[1] | Days on Test Run | Conversion[2] | Selectivity[3] |
|---|---|---|---|---|
| 22 (twice regenerated) | 1.0 | 3.4 | 61 | 94 |

[1]Weight hourly space velocity of propylene feedstock.
[2]Average conversion in percent of propylene converted.
[3]Percent of products existing as propylene dimer.

EXAMPLE 23

A quantity of catalyst material for use in the present invention was prepared as in Example 4. The calcined catalyst material thus prepared was shown by analysis to contain 2.5 weight percent Ni and 1.3 weight percent S. The catalyst material was then diluted by mixing with a quantity of tabular alumina so that the ratio of catalyst material of Example 23 to non-catalytic tabular alumina was 5.24 to 1.

The diluted nickel sulfate impregnated catalyst material prepared in Example 23 was evaluated in the same testing method used for the catalyst material of Example 21 (nickel chloride impregnated catalyst). The feedstock comprised 64.7 weight percent propylene and 35.3 weight percent propane until about 40 hours, when it was changed to contain 67.4 weight percent propylene, remainder propane. At various times during the test, the catalyst bed temperature, weight hourly space velocity of propylene feed, percent conversion of propylene feed and percent propylene dimer selectivity were measured and recorded. All data from this test appear in Table III.

TABLE III

Aging/Regeneration Study of Catalyst Material of Example 23 in Present Process

| Days on Test Run | Temp, °F | WHSV[1] | Conversion[2] | Selectivity[3] |
|---|---|---|---|---|
| 0.2 | 106 | 0.45 | | |
| 1.2 | 107 | 0.45 | 99.6 | 62.9 |
| 2.0 | 101 | 0.50 | 99.1 | 76.6 |
| 5.1 | 106 | 0.49 | | |
| 6.0 | 106 | 0.49 | 99.0 | 84.0 |
| 9.0 | 106 | 0.39 | 98.8 | 85.3 |
| 11.4 | 107 | 0.36 | 99.2 | 84.7 |
| 13.4 | 107 | 0.37 | | |
| 14.4 | 107 | 0.45 | | |
| 15.4 | 108 | 0.65 | 98.5 | 86.6 |
| 18.4 | 107 | 0.42 | 99.1 | 85.4 |
| 22.4 | 107 | 0.47 | 98.7 | 86.9 |
| 25.4 | 107 | 0.49 | 98.7 | 85.7 |
| 26.4 | 107 | 0.49 | | |
| 27.4 | 107 | 0.38 | | |
| 28.4 | 107 | 0.47 | 98.5 | 87.0 |
| 29.5 | 107 | 0.37 | | |
| 32.4 | 106 | 0.38 | 98.6 | 86.6 |
| 35.4 | 107 | 0.43 | | |
| 38.0 | 107 | 0.43 | 98.5 | 85.4 |
| 39.9 | 107 | 0.53 | | |
| 42.0 | 106 | 0.54 | 97.8 | 86.9 |
| 45.2 | 106 | 0.44 | | |
| 46.9 | 107 | 0.47 | | |
| 48.2 | 107 | 0.49 | | |
| 50.0 | 107 | 0.48 | 97.1 | 87.9 |
| 52.0 | 107 | 0.49 | 97.0 | 88.5 |
| 53.0 | 108 | 0.44 | 96.8 | 88.5 |
| 55.0 | 107 | 0.49 | 96.3 | 89.0 |
| 58.0 | 107 | 0.51 | 94.6 | 89.7 |
| 59.0 | 107 | 0.50 | 94.4 | 89.7 |
| 59.9 | 105 | 0.39 | | |
| (Temperature Increased) | | | | |
| 61.0 | 127 | 0.54 | 95.4 | 86.8 |
| 62.0 | 126 | 0.36 | 95.9 | 87.0 |
| 63.0 | 126 | 0.44 | 95.0 | 86.8 |
| 65.0 | 126 | 0.48 | 94.6 | 87.2 |
| 67.0 | 126 | 0.49 | 93.1 | 86.3 |
| 68.0 | 127 | 0.36 | 93.3 | 88.8 |
| 70.0 | 127 | 0.40 | 91.9 | 89.7 |
| 71.9 | 127 | 0.53 | 89.3 | 88.6 |
| (Temperature Increased) | | | | |
| 73.0 | 150 | 0.40 | 92.0 | 87.8 |
| 74.0 | 150 | 0.55 | 87.9 | 89.0 |
| 75.0 | 151 | 0.40 | 87.8 | 89.3 |
| 76.0 | 150 | 0.44 | 83.9 | 90.8 |
| 77.0 | 150 | 0.36 | 83.5 | 90.5 |
| (Catalyst Regenerated)[4] | | | | |
| 0.1 | 109 | 0.45 | | |
| 0.9 | 109 | 0.40 | 99.3 | 78.8 |
| 1.9 | 108 | 0.36 | 99.3 | 82.9 |
| 3.1 | 108 | 0.38 | | |
| 3.9 | 108 | 0.47 | 99.1 | 85.7 |
| 4.6 | 109 | 0.45 | | |
| 5.6 | 108 | 0.41 | 99.4 | 84.1 |
| 6.5 | 108 | 0.50 | | |
| (Temperature Increased) | | | | |
| 7.6 | 129 | 0.36 | 99.5 | 81.7 |
| 8.5 | 129 | 0.42 | | |
| 9.3 | 129 | 0.43 | 99.6 | 83.0 |

[1]Weight hourly space velocity of propylene feedstock.
[2]Average conversion in percent of propylene converted.
[3]Percent of products existing as propylene dimer.
[4]Regeneration by steps of (a) purging overnight at 550°F with helium, (b) replacing helium with air at 50cc/minute/cc of catalyst, (c) heating rapidly in air to 950°F, (d) holding for 20 minutes at 950°F, (e) replacing air with helium for 2 hours at 950°F.

It is clear from the above that the catalyst for use in the present process, i.e. one having the specific limited range of properties as above defined, is capable of affording high yield of desired products and is easily and effectively regenerated without loss in activity. It is also clear from the above that the prior art catalyst giving comparable product yield when fresh, fails to perform upon regeneration as well as the present catalyst.

Because the catalyst for use in the present process will withstand numerous regenerations without loss in activity, it is contemplated that a catalyst life in commercial application may be as long as 2 years or more.

It will be appreciated that the examples set forth hereinbefore are merely illustrative and that the operation conditions for the dimerization reaction in accordance with the process of this invention, as exemplified in the foregoing examples, may be varied within the limits specified and that various modifications and alterations may be made in the process of this invention without departing from the spirit and scope thereof.

What is claimed is:

1. In a method for dimerization of an olefin feed of 2 to 4 carbon atoms which comprises contacting said olefin under olefin dimerization conditions including a temperature of from about 32°F to about 350°F, a pressure of from about 200 psig to about 1000 psig and an olefin weight hourly space velocity of from about 0.1 to about 10 with a catalyst of alumina selected from the group consisting of gamma alumina, eta alumina and a mixture thereof having intimately combined therewith nickel and sulfur as a result of impregnation with nickel sulfate, the improvement wherein said catalyst of alumina has intimately combined therewith from about 2 to about 5 weight percent nickel and from about 1 to about 3 weight percent sulfur, and has been calcined at a temperature of from 750°F to about 1150°F in an inert non-reducing atmosphere.

2. The improvement of claim 1 wherein said olefin is propylene.

3. The improvement of claim 1 wherein said catalyst of alumina has intimately combined therewith from about 2 to about 3 weight percent nickel and from about 1 to about 1.7 weight percent sulfur.

4. The improvement of claim 1 wherein said contacting is conducted at an olefin weight hourly space velocity of from about 0.2 to about 4, a temperature of from about 100°F to about 200°F and a pressure of from about 250 psig to about 600 psig.

5. The improvement of claim 3 wherein said contacting is conducted at an olefin weight hourly space velocity of from about 0.2 to about 4, a temperature of from about 100°F to about 200°F and a pressure of from about 250 psig to about 600 psig.

6. The improvement of claim 5 wherein said olefin is propylene.

7. The improvement of claim 1 wherein said olefin feed is a mixture of olefin of 2 to 4 carbon atoms and one or more non-reactive organic compounds selected from the group consisting of saturated straight chain hydrocarbons of 3 to 10 carbon atoms.

8. The improvement of claim 7 wherein said olefin is propylene and said non-reactive compound is selected from the group consisting of propane, butane and n-hexane.

9. The improvement of claim 8 wherein said nonreactive compound is propane.

10. The improvement of claim 7 wherein said catalyst is in mixture with a non-catalytic diluting agent selected from the group consisting of inorganic oxides and clay.

11. The improvement of claim 10 wherein said non-catalytic diluting agent is selected from the group consisting of alumina, zirconia, silica, magnesia, thoria, titania, boria, bentonite clay, kieselguhr clay and combinations thereof.

* * * * *